United States Patent
Planas et al.

(10) Patent No.: US 10,254,916 B2
(45) Date of Patent: Apr. 9, 2019

(54) SYSTEMS AND METHODS FOR MONITORING AND CORRECTING DEFECTS AND TUBING INSTALLATION ERRORS FOR BLOOD PROCESSING SYSTEMS

(71) Applicant: Fenwal, Inc., Lake Zurich, IL (US)

(72) Inventors: Samantha M. Planas, Wauconda, IL (US); Kathleen M. Higginson, Mount Prospect, IL (US); Amit J. Patel, Algonquin, IL (US)

(73) Assignee: Fenwal, Inc., Lake Zurich, IL (US)

( * ) Notice: Subject to any disclaimer, the term of this patent is extended or adjusted under 35 U.S.C. 154(b) by 619 days.

(21) Appl. No.: 14/753,550

(22) Filed: Jun. 29, 2015

(65) Prior Publication Data
US 2016/0378298 A1  Dec. 29, 2016

(51) Int. Cl.
*G06F 3/0481* (2013.01)
*A61M 1/02* (2006.01)
*A61M 1/30* (2006.01)
*A61M 1/36* (2006.01)
*A61M 1/38* (2006.01)
*G06F 3/0484* (2013.01)
*G16H 40/63* (2018.01)

(52) U.S. Cl.
CPC .......... *G06F 3/04817* (2013.01); *A61M 1/02* (2013.01); *A61M 1/30* (2013.01); *A61M 1/36* (2013.01); *A61M 1/3663* (2013.01); *A61M 1/38* (2013.01); *G06F 3/0484* (2013.01); *A61M 2205/502* (2013.01); *A61M 2205/505* (2013.01); *G16H 40/63* (2018.01)

(58) Field of Classification Search
CPC ............ A61B 1/00009; A61B 1/00039; A61B 1/00045; A61B 2017/00119; A61B 5/02042; A61B 5/742
See application file for complete search history.

(56) References Cited

U.S. PATENT DOCUMENTS 3,935,876 A    2/1976  Massie et al.
4,673,927 A    6/1987  Cianciavicchia et al.
(Continued)

FOREIGN PATENT DOCUMENTS

EP          0522527         1/1993
WO      WO 2012/125457      9/2012

OTHER PUBLICATIONS

"Dialog Dialsis Machine", Braun Sharing Expertise, May 2010.*

*Primary Examiner* — Namitha Pillai
(74) *Attorney, Agent, or Firm* — Cook Alex Ltd.

(57) ABSTRACT

A system is provided for processing blood from a blood source. The system cooperates with a disposable fluid flow circuit including a tubing line that is associated with a clamp of the system. The system also includes a sensor and a controller, which cooperate to determine whether the fluid flow circuit and/or the system itself is defective and/or if the fluid flow circuit has been installed onto the system improperly. If such an error or defect exists, then the controller determines whether a selected system state exists. The controller causes a change in the appearance of the display of the system, which includes displaying an interactive icon if the selected system state exists. The icon, when manipulated, causes the clamp to move from the closed condition to an open condition.

33 Claims, 8 Drawing Sheets

(56) References Cited

U.S. PATENT DOCUMENTS

| | | | |
|---|---|---|---|
| 5,194,145 | A | 3/1993 | Schoendorfer |
| 5,234,608 | A | 8/1993 | Duff |
| 5,964,724 | A | 10/1999 | Rivera et al. |
| 6,531,708 | B1 | 3/2003 | Malmstrom et al. |
| 6,750,468 | B2 | 6/2004 | Malmstrom et al. |
| 7,789,245 | B2 | 9/2010 | Westberg et al. |
| 8,442,607 | B2 * | 5/2013 | Banet ................ A61B 5/02055 600/310 |
| 2002/0032398 | A1 | 3/2002 | Steele et al. |
| 2002/0151804 | A1 | 10/2002 | O'Mahony et al. |
| 2002/0179544 | A1 | 12/2002 | Johnson et al. |
| 2003/0214412 | A1 | 11/2003 | Ho et al. |
| 2008/0149551 | A1 | 6/2008 | Brugger et al. |
| 2009/0012455 | A1 | 1/2009 | Childers et al. |
| 2010/0175483 | A1 | 7/2010 | O'Mahony et al. |
| 2012/0123322 | A1 | 5/2012 | Scarpaci et al. |
| 2012/0289928 | A1 | 11/2012 | Wright et al. |

* cited by examiner

SYSTEMS AND METHODS FOR
MONITORING AND CORRECTING
DEFECTS AND TUBING INSTALLATION
ERRORS FOR BLOOD PROCESSING
SYSTEMS

BACKGROUND

Field of the Disclosure

The invention relates to blood processing systems. More particularly, the invention relates to systems and methods for monitoring and correcting defects in a disposable fluid flow circuit or blood processing system and installation errors.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., which is an affiliate or Fresenius Kabi AG or Bad Homburg, Germany, or other centrifugal separation devices, or a spinning membrane-type separator, such as the AUTOPHERESIS-C® and AURORA® devices from Fenwal, Inc.

Typically, a disposable fluid flow circuit is provided for use in combination with a durable, reusable blood processing system. The fluid flow circuit includes a plurality of components (e.g., fluid storage bags and separation chambers) connected by tubing lines, which must be properly installed onto the blood processing system. Known systems may include an alert or alarm system that is programmed to generate an alert or alarm when there is a problem with the blood processing system or fluid flow circuit (e.g., if it has been improperly installed onto the blood processing system), but there remains room for improvement in such alarm systems and the ways in which an improperly installed or defective fluid separation system event may be resolved.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a graphical user interface of a durable blood processing system including a clamp and configured for use in combination with a disposable fluid flow circuit including a tubing line associable with the clamp is provided. The graphical user interface includes a display and a controller associated with the display. The controller is programmed to determine the existence of an error in the way in which the fluid flow circuit is associated with the blood processing system and/or a defect in the fluid flow circuit and/or blood processing system. Upon determining the existence of such an error and/or defect, the controller determines whether a selected system state exists and causes a change in the appearance of the display to represent the existence of the error and/or defect. If the selected system state exists, the change in the appearance of the display includes displaying an interactive icon on the display that may be manipulated to cause the clamp to be moved from a closed condition to an open condition.

In another aspect, a blood processing system is provided for use in combination with a disposable fluid flow circuit including a tubing line. The blood processing system includes a clamp, a controller, a sensor, and a graphical user interface having a display. The clamp is configured to be associated with the tubing line of the fluid flow circuit and be movable between a closed condition in which fluid flow through the tubing line is prevented and an open condition in which fluid flow through the tubing line is allowed. The sensor, clamp, and display are associated with the controller, which is programmed to receive a signal from the sensor that is indicative of the existence of an error in the way in which the fluid flow circuit is associated with the blood processing system and/or a defect in the fluid flow circuit and/or blood processing system. Upon receiving the signal from the sensor, the controller determines whether a selected system state exists. The controller also causes a change in the appearance of the display to represent the existence of said error and/or defect and, if the selected system state exists, the change in the appearance of the display includes displaying an interactive icon on the display that may be manipulated to cause the clamp to be moved from the closed condition to the open condition.

In yet another aspect, a method is provided for monitoring the combination of a durable blood processing system including a clamp and a disposable fluid flow circuit including a tubing line associated with the clamp. The method includes determining the existence of an error in the way in which the fluid flow circuit is associated with the blood processing system and/or a defect in the fluid flow circuit and/or blood processing system. Upon determining the existence of such an error and/or defect, it is determined whether a selected system state exists and, if the selected system state exists, an interactive icon is displayed. The icon may be manipulated to cause the clamp to be moved from a closed condition to an open condition.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

According to an aspect of the present disclosure, a durable or reusable blood processing system is used in combination with a separate fluid flow circuit, which may be disposable. In the exemplary embodiment illustrated and described herein, the blood processing system is provided as a blood separation or apheresis system, which may separate blood into two or more constituent components (e.g., separating blood into cell-free plasma and concentrated cellular components), but a differently configured and functioning blood processing system may also be provided without departing from the scope of the present disclosure. For example, rather than being configured as an apheresis system, a blood processing system according to the present disclosure may be configured to process blood in a different way, such as by providing a blood processing system that is configured for dialysis or pathogen inactivation or the like.

Figure 1:
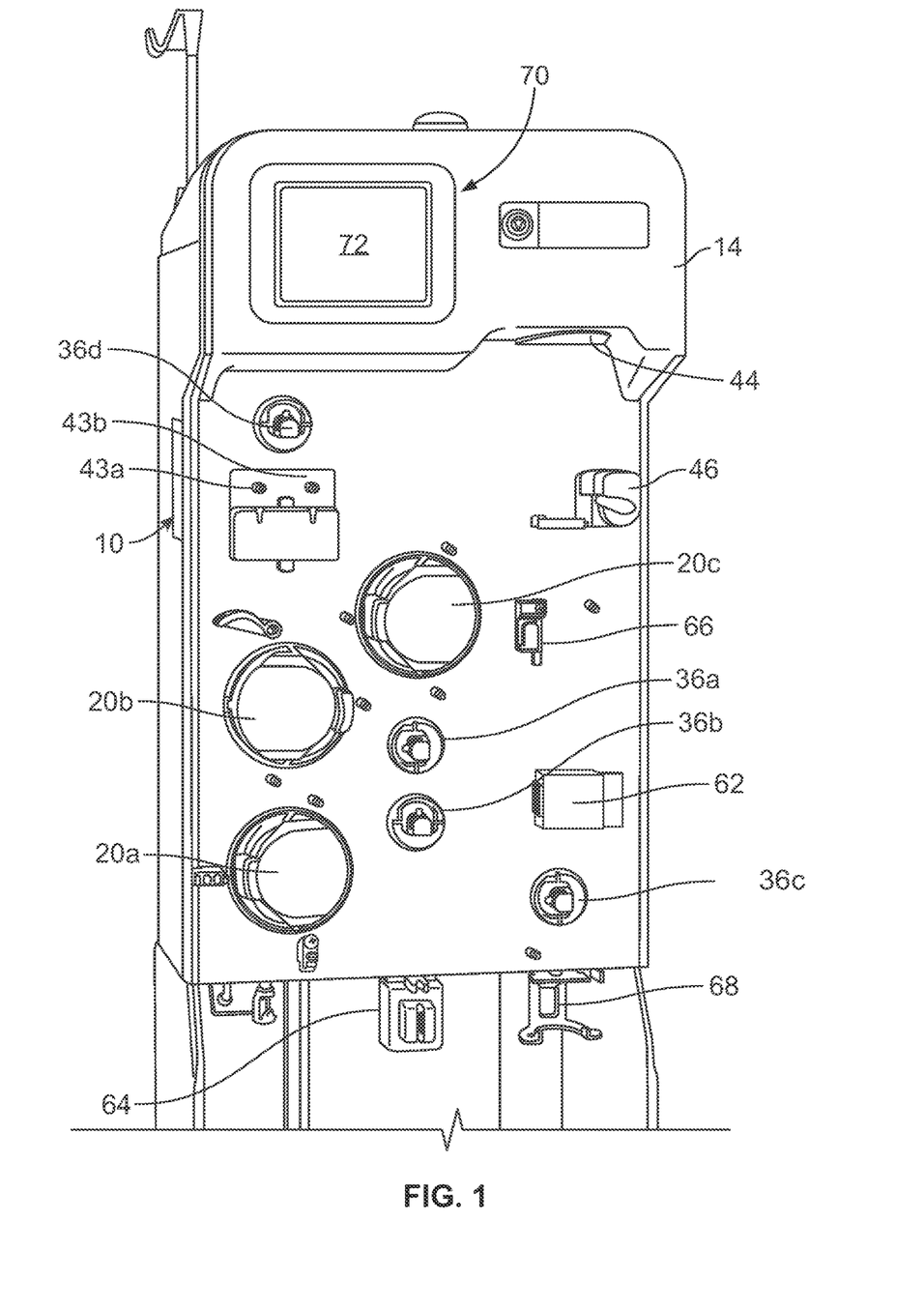
FIG. 1 is a front perspective view of an exemplary blood processing system according to an aspect of the present disclosure.
Figure 2:
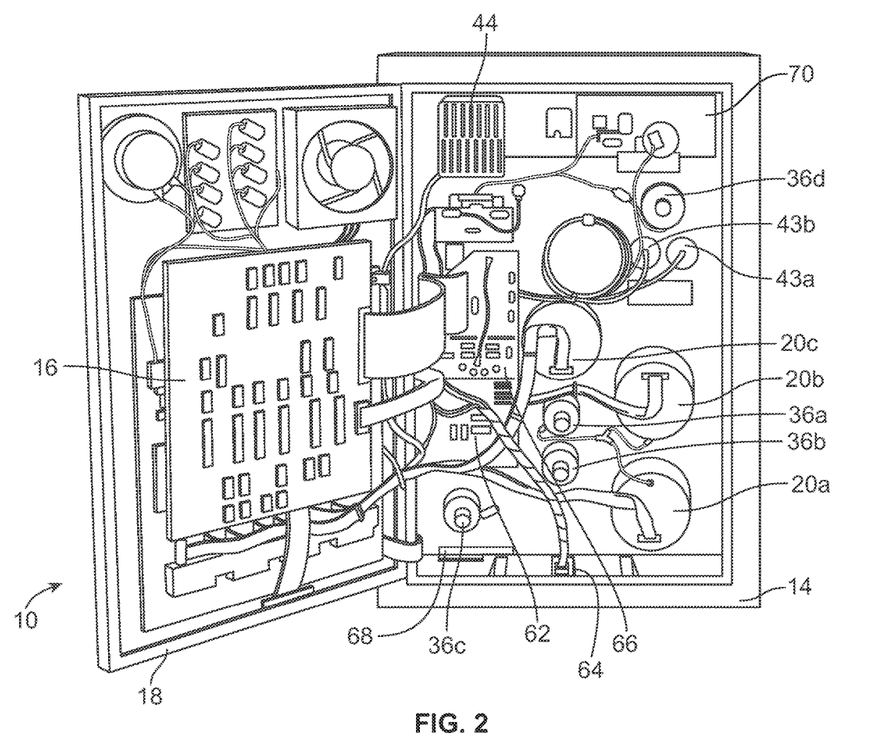
FIG. 2 is a rear perspective view of the blood processing system of FIG. 1, with a rear door thereof in an open position.
Figure 3:
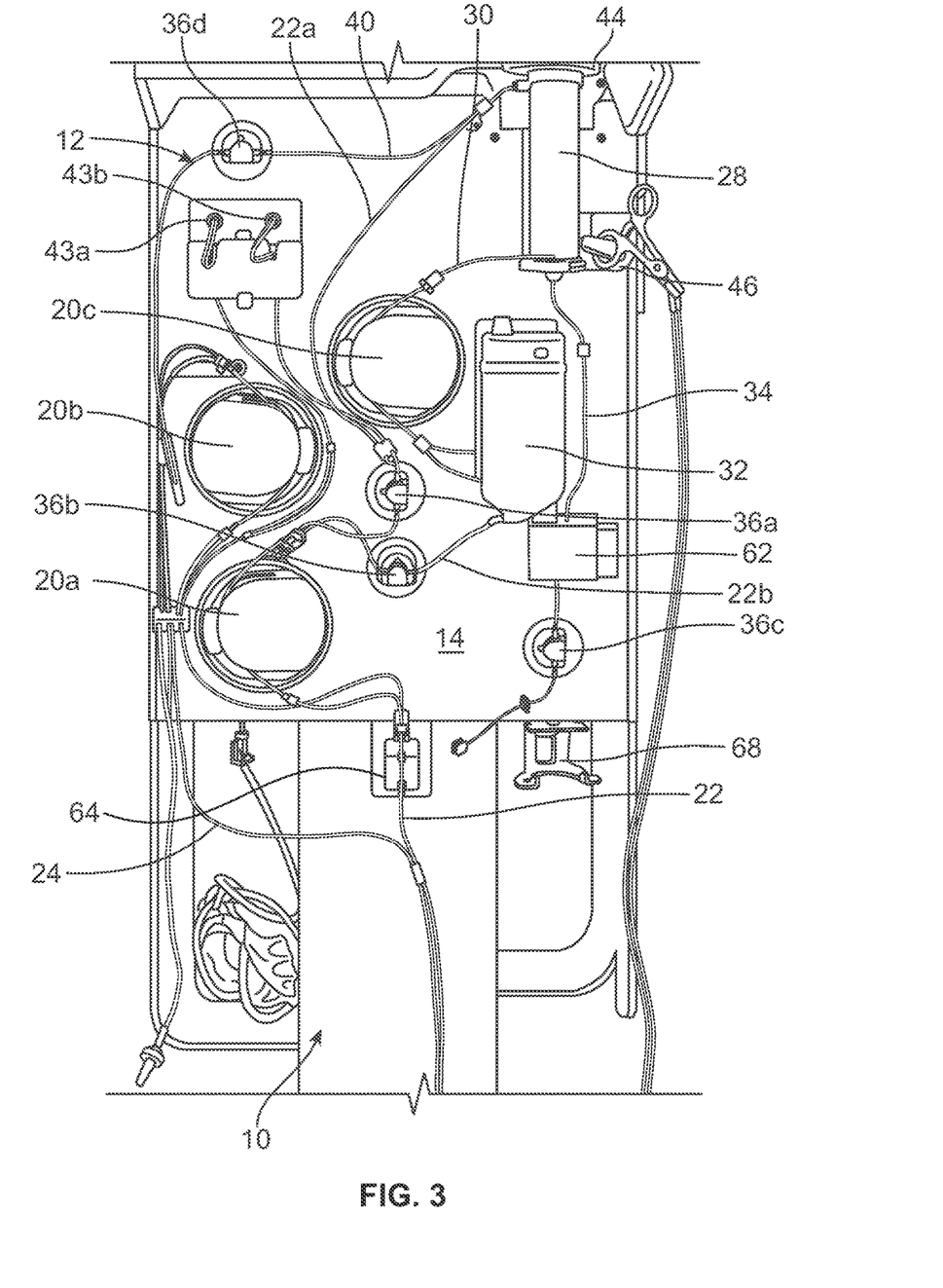
FIG. 3 is a front perspective view of the blood processing system of FIG. 1, with a fluid flow circuit associated therewith.

FIGS. 1 and 2 illustrate an exemplary blood processing system 10, while FIG. 3 illustrates an exemplary fluid flow circuit 12 mounted onto the blood processing system 10. However, as described above, it should be understood that the illustrated blood processing system 10 is merely exemplary and may be differently configured without departing from the scope of the present disclosure. The configuration of the fluid flow circuit 12 depends upon the configuration of the blood processing system 10, so it should be understood that varying the function and/or configuration of the blood processing system 10 may necessitate a differently configured fluid flow circuit 12 as well.

The exemplary system 10 of FIG. 1 is configured for processing whole blood, but it may be used to process any other plasma-containing fluid to separate plasma from concentrated fluid (which may be red cell concentrate or packed red cells when the plasma-containing fluid constitutes whole blood). The plasma-containing fluid may come from any fluid source, which may include a living donor or patient (e.g., a human blood donor) or a non-living source (e.g., a blood bag or fluid container).

Figure 5:
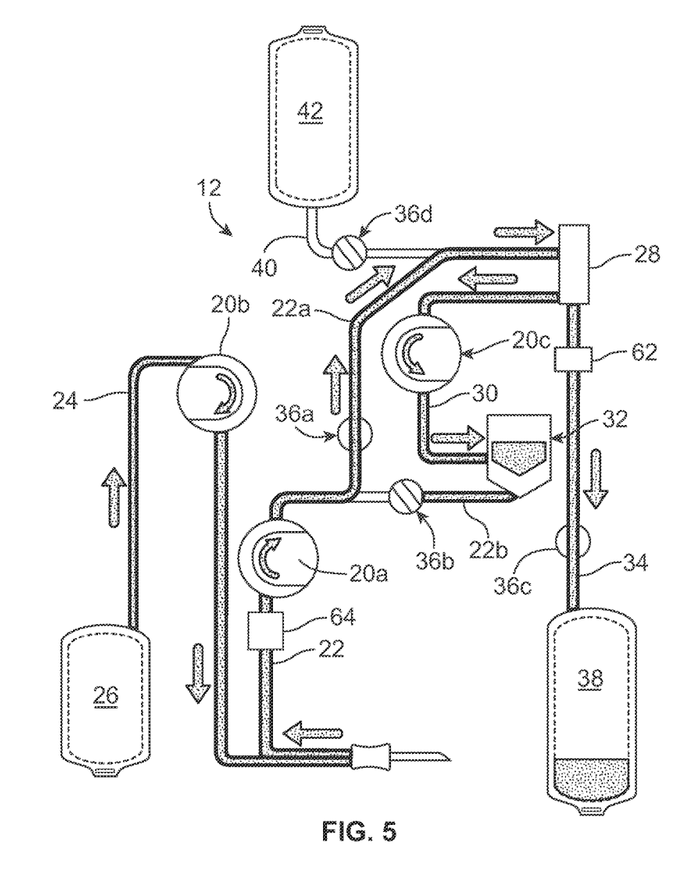
FIG. 5 is a schematic view of the fluid flow circuit and blood processing system of FIG. 3, in a fluid draw mode.
Figure 6:
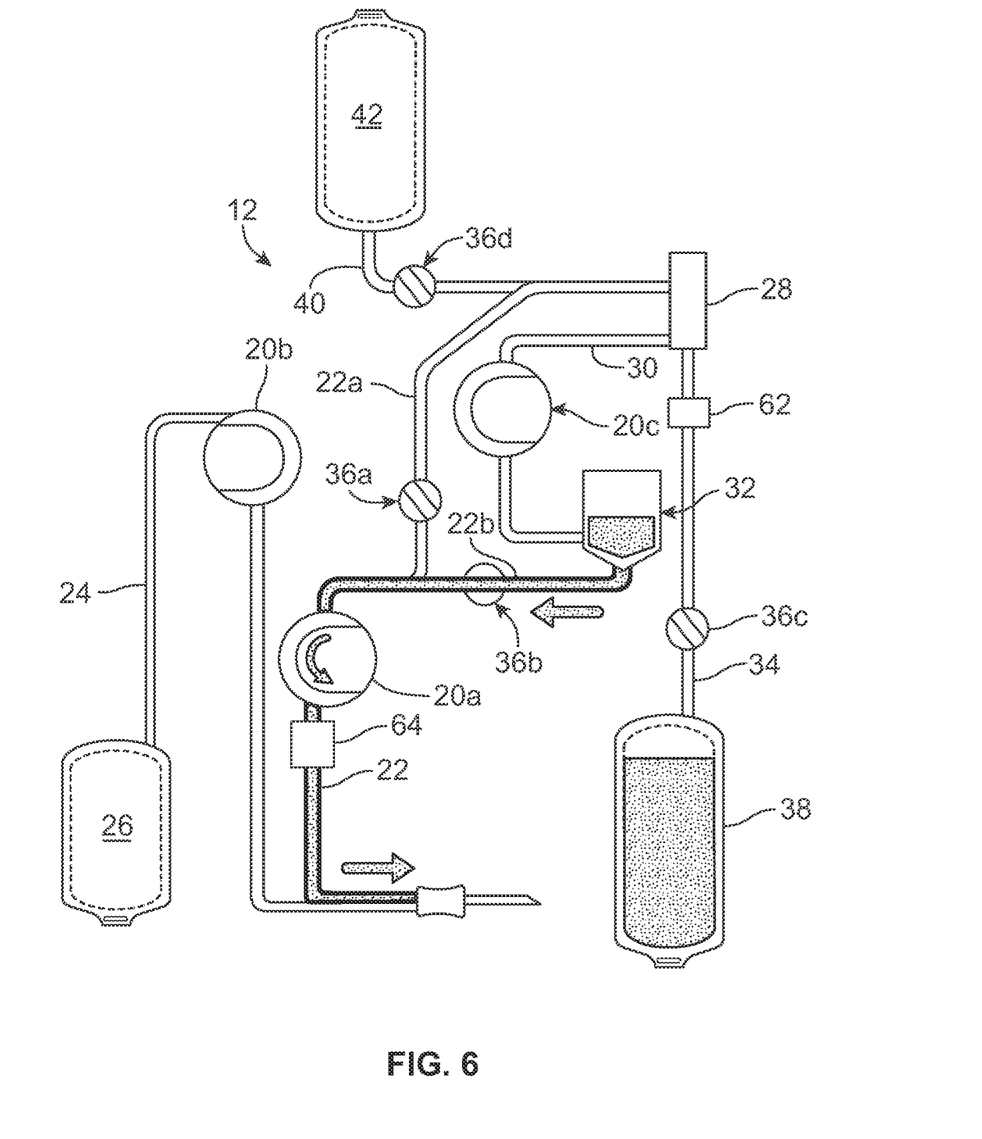
FIG. 6 is a schematic view of the fluid flow circuit and blood processing system of FIG. 3, in a fluid return mode.

The illustrated system 10 includes a cabinet or housing 14, with several components positioned outside of the cabinet 14 (e.g., associated with a front wall or surface or panel of the cabinet 14) and additional components (including a central processing unit or controller 16) and interconnects positioned inside of the cabinet 14, which may be accessed by opening a rear door 18 of the system 10, as shown in FIG. 2. It should be understood that the illustrated system components and the location of the components is merely exemplary, and that additional or different components and different component arrangements may be incorporated into the system without departing from the scope of the present disclosure. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump, which may be associated with a source/recipient access line 22 of the fluid flow circuit 12 and operates to draw fluid from a fluid or blood source (FIG. 5) and to return fluid to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid or blood separation module or chamber 28 of the fluid flow circuit 12. A third pump 20c may be provided as a concentrated fluid pump, which may be associated with a concentrated fluid outlet line 30 and operates to draw concentrated fluid from the fluid separation chamber 28 and direct it into a concentrated fluid reservoir 32 after the plasma-containing fluid has been separated into a concentrated fluid and separated plasma in the fluid separation chamber 28.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a plasma outlet line 34 of the fluid flow circuit 12 to draw separated plasma from the fluid separation chamber 28 after the plasma-containing fluid has been separated into a concentrated fluid and separated plasma. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps 36a-36d associated with the tubing lines of the fluid flow circuit 12 and movable between open and closed conditions under command of the controller 16. The clamps 36a-36d may be variously configured and operate to selectively allow and prevent fluid flow through the associated tubing line. In the illustrated embodiment, one clamp 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps 36b may be provided as a reinfusion clamp, which may be associated with a reinfusion branch 22b of the source/recipient access line 22 downstream of a concentrated fluid reservoir 32 of the fluid flow circuit 12 to allow (FIG. 6) or prevent (FIG. 5) the flow of concentrated fluid through the reinfusion branch 22b. A third clamp 36c may be provided as a plasma clamp, which may be associated with the plasma outlet line 34 to allow (FIG. 5) or prevent (FIG. 6) the flow of separated plasma through the plasma outlet line 34 and into a separated plasma container 38. A fourth clamp 36d may be provided as a replacement fluid clamp, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps 36a-36d to act so as to alleviate the improper pressure condition (e.g., by reversing the direction of operation of one of the pumps 20a-20c and/or opening or closing one of the clamps 36a-36d). Additional or alternative pressure sensors may also be provided without departing from the scope of the present disclosure.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a plasma-containing fluid to enter into the housing 48 (via the draw branch 22a of the source/recipient access line 22), while a side outlet 54 allows concentrated fluid to exit the housing 48 (via the concentrated fluid outlet line 30) and a bottom outlet 56 allows separated plasma to exit the housing 48 (via the plasma outlet line 34) after the plasma-containing fluid has been separated into concentrated fluid and plasma.

Figure 4:
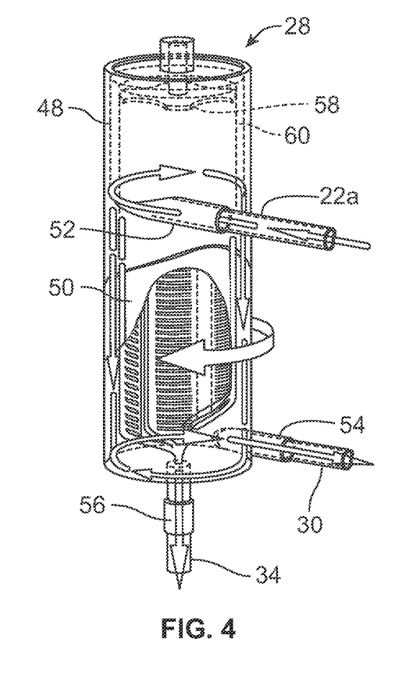
FIG. 4 is a front perspective view of a blood separation chamber of the fluid flow circuit of FIG. 3, with a portion thereof broken away for illustrative purposes.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the concentrated fluid (which may be cellular blood components) away from the membrane 50 to exit the fluid separation chamber 28 via the side outlet 54, while the separated plasma passes through the membrane 50 toward the central axis of the housing 48 to exit the fluid separation chamber 28 via the bottom outlet 56. It should be understood that the present disclosure is not limited to a particular fluid separation chamber and that the illustrated and described fluid separation chamber 28 is merely exemplary. For example, in other embodiments, a centrifugal device that separates fluid components based on density, rather than size, may be employed to separate a plasma-containing fluid into plasma and a concentrated fluid.

The system 10 further includes a hemoglobin detector or optical sensor assembly 62 associated with the plasma outlet line 34 when the fluid flow circuit 12 has been installed on the system 10. The optical sensor assembly 62 is used to determine the concentration of free plasma hemoglobin in the separated plasma flowing through the plasma outlet line 34 (and may also detect other irregularities in the plasma outlet line 34, such as red blood cells, lipids, and air bubbles) and may be variously configured. In one embodiment, the optical sensor assembly 62 includes a red light source and a green light source, which may be provided as light-emitting diodes. The optical sensor assembly 62 may also include at least one light detector or sensor that is configured and oriented to receive light from one or both of the light sources. The optical sensor assembly 62 may include a cover or housing that blocks ambient light from reaching the detector(s) and/or one or more mirrors or reflective elements that maximize the light from the light sources that reaches the detector(s).

An exemplary system using red and green light to detect the presence of free plasma hemoglobin in separated plasma and determining its concentration is described in greater detail in U.S. Pat. No. 7,789,245, which is hereby incorporated herein by reference. It should be understood that this is only one system for detecting the presence of free plasma hemoglobin in separated plasma and determining its concentration and that any other suitable system and method for determining the concentration of free plasma hemoglobin in separated plasma may be employed without departing from the scope of the present disclosure. Additionally, the system 10 may include other optical sensors (including, for example, a bar code reader) that are configured and oriented to be associated with other tubing lines and components of the fluid flow circuit 12 to monitor any of a number of characteristics of the associated tubing line or circuit components and/or the fluid flowing through the associated tubing line or circuit component.

According to one method of using the fluid separation system 10 and fluid flow circuit 12, a plasma-containing fluid (e.g., blood) is drawn from a fluid or blood source into the fluid separation chamber 28 during a draw phase or mode (FIG. 5), where it is separated into concentrated fluid and separated plasma. The separated plasma is retained by the system 10, while the concentrated fluid is returned to a fluid recipient during a return or reinfusion phase or mode (FIG. 6). In one embodiment, the draw and return phases are repeatedly alternated (drawing from the fluid source, separating the fluid into plasma and concentrated fluid, and then returning the concentrated fluid to the fluid recipient) until a target (e.g., a collected amount of separated plasma) is achieved. All of the draw phases and all of the return phases may be identical or may differ from each other. For example, a final draw phase may draw less fluid from the fluid source than the previous draw phases and a final return phase may infuse a combination of concentrated fluid and replacement fluid to the fluid recipient, whereas the previous return phases return only concentrated fluid to the fluid recipient.

Figure 7:
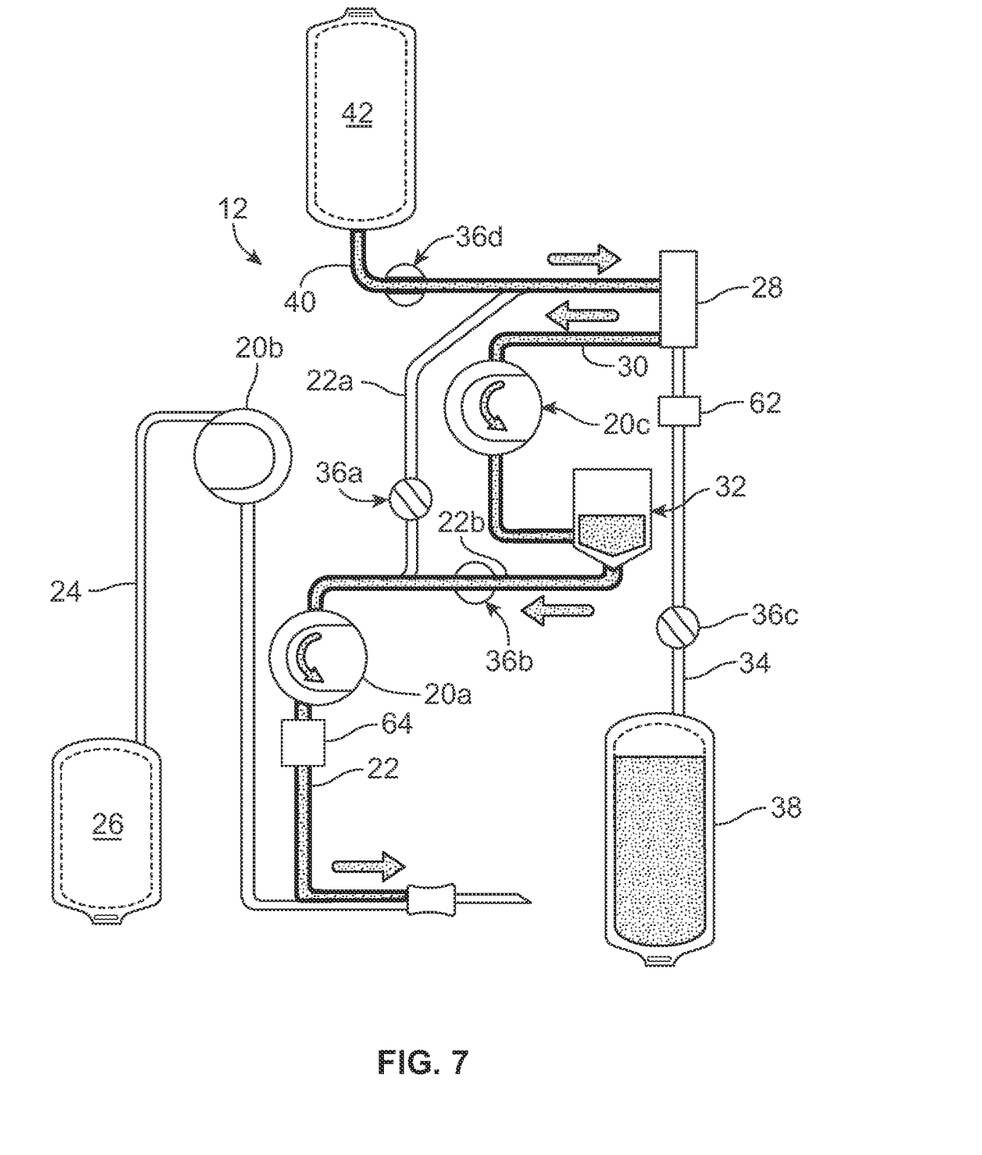
FIG. 7 is a schematic view of the fluid flow circuit and blood processing system of FIG. 3, in a replacement fluid return mode.

FIG. 7 shows an exemplary phase or mode in which replacement fluid (e.g., saline) is directed to the fluid recipient, either alone or with an amount of concentrated fluid. In the phase of FIG. 7, the clamp 36d associated with the replacement fluid line 40 is opened to allow replacement fluid to flow out of the replacement fluid source 42. The clamp 36a associated with the draw branch 22a of the source/recipient access line 22 may be in a closed condition to prevent fluid flow therethrough, such that the replacement fluid is directed into the fluid separation chamber 28. The replacement fluid is pulled out of the fluid separation chamber 28 and into the concentrated fluid reservoir 32 by operation of the pump 20c associated with the concentrated fluid outlet line 30. If there is any concentrated fluid in the concentrated fluid reservoir 32, then the replacement fluid mixes with the concentrated fluid prior to being pumped to the fluid recipient by the pump 20a associated with the source/recipient access line 22, otherwise the replacement fluid alone may be pumped to the fluid recipient. In one embodiment, the replacement fluid return mode of FIG. 7 is carried out only once, as a final return phase (e.g., when the amount of concentrated fluid in the concentrated fluid reservoir 32 is at a sufficiently low level) in which a mixture of concentrated fluid and replacement fluid is returned to the fluid recipient. This may be advantageous to ensure that all of the concentrated fluid in the concentrated fluid reservoir 32 (along with any remaining in the fluid separation chamber 28) is rinsed out of the concentrated fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber 28 and the concentrated fluid reservoir 32 if the replacement fluid is being pumped to a fluid recipient earlier in the procedure. In this case, the clamp 36d associated with the replacement fluid line 40 and the clamp 36a associated with the draw branch 22a of the source/recipient access line 22 may be opened to allow fluid flow therethrough, with the clamp 36b associated with the reinfusion branch 22b in a closed condition to prevent fluid flow therethrough. The pump 20a associated with the source/recipient access line 22 may be activated (with the other two pumps 20b and 20c inactive) to draw replacement fluid out of the replacement fluid source 42 and through the replacement fluid line 40, the draw branch 22a, and finally the source/recipient access line 22 to the fluid recipient.

The concentrated fluid and/or replacement fluid being returned to the fluid recipient may be monitored to detect the presence of air. Detection of air in a fluid return line of a blood processing system is known, and any suitable air detection assembly may be incorporated into blood processing systems according to the present disclosure. In the illustrated embodiment, an air detection assembly 64 of the blood processing system 10 is part of the front panel of the cabinet 14, and configured to receive a portion of the reinfusion branch 22b of the source/recipient access line 22. The illustrated air detection assembly 64 is positioned downstream of the source/recipient access pump 20a (i.e., between the source/recipient access pump 20a and the fluid recipient), with the source/recipient access pump 20a being positioned between the concentrated fluid reservoir 32 and the air detection assembly 64 when the fluid flow circuit 12 has been mounted onto the blood processing system 10.

In one embodiment, the air detection assembly 64 may be provided as an ultrasonic monitoring device or acoustic sensor, with at least one sound wave emitter and at least one sound wave receiver positioned on opposite sides of the source/recipient access line 22. An ultrasonic sound wave will travel through fluid (e.g., concentrated fluid and/or replacement fluid) substantially unimpeded, whereas an ultrasonic sound wave traveling through an air bubble will arrive at the receiver with a reduced magnitude. The air detection assembly 64 may be associated with the system controller 16, which may issue instructions to the air detection assembly 64 (e.g., instructing the sound wave emitter and receiver when to be operative) and receive signals or outputs generated by the air detection assembly 64 (e.g., receiving an output of the sound wave receiver that is indicative of the contents of the reinfusion branch 22b of the source/recipient access line 22 passing through the air detection assembly 64). If the controller 16 receives an output from the sound wave receiver that is indicative of a low magnitude sound wave, then the controller may interpret the output as signifying the presence of air in the source/recipient access line 22. In other embodiments, other air detection assembly configurations (e.g., an optical monitor) and/or methods for detecting air in the source/recipient access line 22 may be employed without departing from the scope of the present disclosure. Additionally, the blood processing system 10 may be provided with other air detection assemblies or acoustic sensors that may be associated with other tubing lines and/or components of the fluid flow circuit 12.

If the air detection assembly 64 detects air in the source/recipient access line 22 moving toward the fluid recipient (e.g., in the return phase of FIG. 6 or the replacement fluid return phase of FIG. 7), then the controller 16 may automatically take steps to remove the air from the source/recipient access line 22. For example, in one embodiment, the controller 16 is programmed to pause or stop the operation of the source/recipient access pump 20a when air is detected in the source/recipient access line 22 moving toward the fluid recipient. If any of the other pumps 20b, 20c are operating, then the controller 16 may either pause operation of them as well or allow them to continue operating, either as before or in a modified capacity. The controller 16 may also generate an alert or an alarm to notify an operator that air is in the source/recipient access line 22 and that the system 10 is taking automated steps to remove the air from the source/recipient access line 22.

The controller 16 may then automatically instruct the source/recipient access pump 20a to operate in a second or reverse direction to move concentrated fluid and/or replacement fluid in the source/recipient access line 22 in a direction away from the fluid recipient to prevent air from being infused into the fluid recipient, which may be harmful if the fluid recipient is a living recipient (e.g., a human). The air detection assembly 64 may continue monitoring the concentrated fluid and/or replacement fluid in the source/recipient access line 22 as the fluid recipient pump 20a operates in the reverse direction to allow the controller 16 to confirm or verify that the air in the source/recipient access line 22 has been passed through the air detection assembly 64 away from the fluid recipient.

The source/recipient access pump 20a continues operating in the reverse or second direction until the air in the source/recipient access line 22 has been removed from the source/recipient access line 22. The location at which the air is removed from the source/recipient access line 22 may vary without departing from the scope of the present disclosure. For example, in the illustrated embodiment, the concentrated fluid and/or replacement fluid in the source/recipient access line 22 may be pumped into the concentrated fluid reservoir 32 at least until the air in the source/recipient access line 22 enters the concentrated fluid reservoir 32. The concentrated fluid reservoir 32 may be a flexible, expandable bag or container, such that air in the concentrated fluid reservoir 32 separates from the concentrated fluid and/or replacement fluid and partially inflates the concentrated fluid reservoir 32, effectively removing the air from the source/recipient access line 22. In other embodiments, the concentrated fluid and/or replacement fluid may be pumped to a different location (e.g., through a dedicated air vent line) to remove the air from the source/recipient access line 22. It may be advantageous for the source/recipient access pump 20a to operate beyond the point that the air in the source/recipient access line 22 has been removed therefrom, by pumping additional concentrated fluid to the air-removal location. By operating beyond the point that the air in the source/recipient access line 22 has been removed, the system 10 may better ensure that the air has been removed.

It may be advantageous for the system 10 to include a separate mechanism to verify that air has been removed from the source/recipient access line 22 as a safety measure. For example, in the illustrated embodiment, the system 10 includes a concentrated fluid weight scale 66 (FIGS. 1 and 2) associated with the concentrated fluid reservoir 32. The concentrated fluid weight scale 66 may weigh the concentrated fluid reservoir 32 and the concentrated fluid and/or replacement fluid contained therein. In one embodiment, the controller 16 monitors the output of the concentrated fluid weight scale 66 to determine that a sufficient amount of concentrated fluid and/or replacement fluid has been pumped back into the concentrated fluid reservoir 32 by the source/recipient access pump 20a so as to clear the air from the source/recipient access line 22. When the controller 16 has verified that the air has been removed from the source/recipient access line 22 (by reference to one or more readings from the concentrated fluid weight scale 66), the controller 16 may instruct the source/recipient access pump 20a to operate in the first or forward direction to move fluid through the source/recipient access line 22 toward and to the fluid recipient. In addition to the concentrated fluid weight scale 66, the system 10 may be provided with additional weight scales configured and oriented to be associated with other components of the fluid flow circuit 12, such as a plasma weight scale 68 configured to be associated with and weigh the separated plasma container 38 and the contents thereof.

The system 10 may be provided with a graphical user interface 70, which is associated with the controller 16 and may be used by an operator to interact with the controller 16. For example, the controller 16 may send signals to the graphical user interface 70 to cause the graphical user interface 70 to display information about a procedure being carried out by the system 10 (e.g., amount of blood drawn from a blood source, time elapsed, etc.), as well as any other information (e.g., time of day), including error alerts. The user may interact with the graphical user interface 70 to provide the controller 16 with information (e.g., the weight of the blood source, if the source is a living donor) and instructions (e.g., instructing the controller 16 to begin a blood separation procedure).

Figure 8:
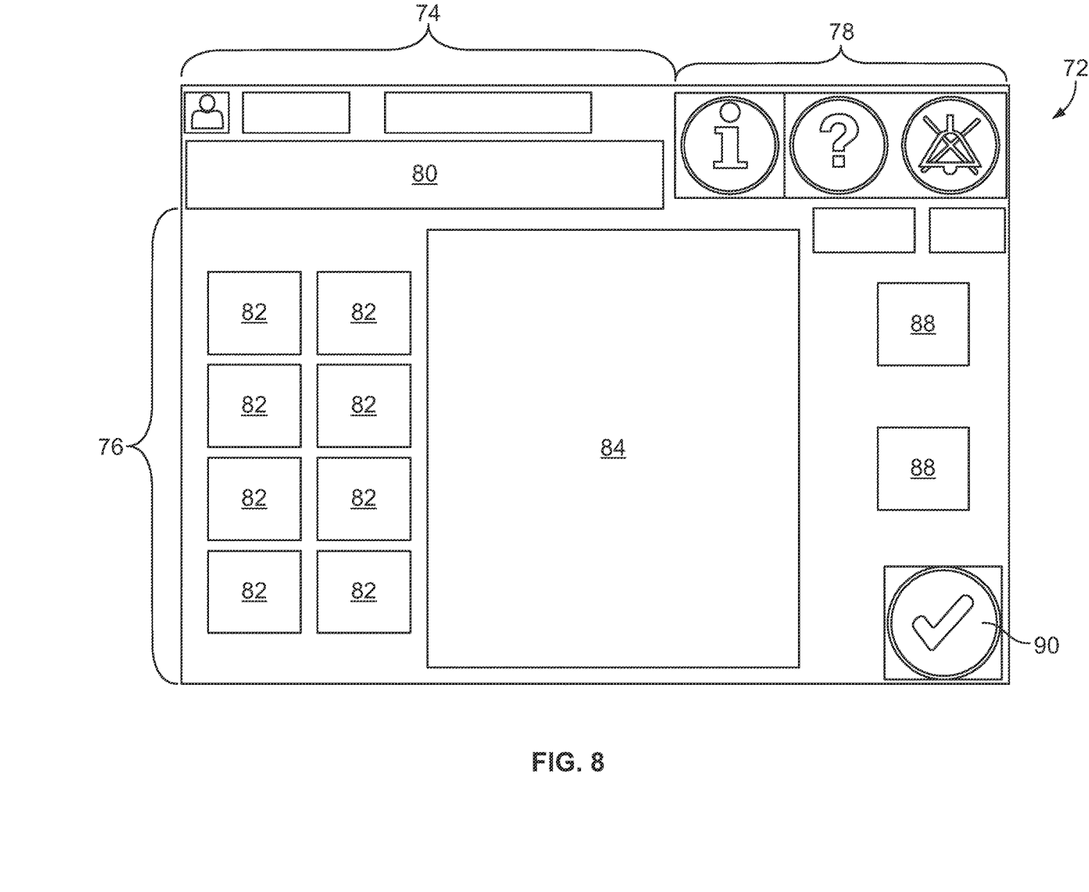
FIG. 8 illustrates an exemplary configuration for the display of a graphical user interface of the blood processing system of FIG. 1.

The illustrated graphical user interface 70 includes a display 72, which is preferably provided as a touchscreen that an operator or technician may directly interact with. FIG. 8 shows an exemplary layout or configuration of the display 72, which may include a plurality of regions intended to serve different functions. For example, one region 74 of the display 72 may be a "Status" region, which may display specific information about the procedure being carried out by the system 10, as well as more general information (e.g., the current time and date). Another region 76 may be a "Task Graphics" region, which may display prompts or visual cues to instruct the operator to perform various tasks (e.g., install the fluid flow circuit 12 onto the system 10 or perform venipuncture). Yet another region 78 may be a "Data" region, which provides interactive icons that may be manipulated by an operator for entering, viewing, and/or modifying data/parameters concerning the blood source and/or the procedure (e.g., adjusting the speed at which one of the pumps 20a-20c operates). Other types of information/prompts and regions may also be incorporated into the display 72 and the various regions of the display 72 may be differently configured and arranged without departing from the scope of the present disclosure.

One of the various functions of the display 72 is to provide notice to the operator of any error/alarm conditions. The graphical user interface 70 and display 72 are associated with the controller 16, which is associated with the various sensors of the system 10 (including the pressure sensors, weight scales, optical sensors, and acoustic sensors described above), which monitor various aspects of the system 10 and associated fluid flow circuit 12. If the controller 16 receives a signal from one of the sensors indicating an error or defect, then the controller 16 may execute any of a number of responses, which may include causing a change in the appearance of the display 72. The change in appearance to represent the existence of an error or defect may include one or more of a change in color of a portion of the display 72, the addition of an icon, the change in shape and/or color of an icon/region/portion of the display 72, or some other visually discernible modification.

In one embodiment, when the controller 16 has determined there to be an error and/or defect, it causes a change in the appearance of several sections of the display 72. The appearance of one or more sections (indicated at 80) may be changed to show text describing the nature of the error/alarm condition and may include an alarm code indicator number or the like. The appearance of other sections of the display 72 (indicated at 82) may be changed to depict recovery actions to be performed by an operator to address the error/defect. These recovery actions may vary according to the nature of the error/defect, but may include actions such as checking a particular portion of the fluid flow circuit 12 to ensure proper installation, checking a sensor of the system 10 to ensure proper functioning, and replacing a defective fluid flow circuit 12 with a new fluid flow circuit 12. The appearance of yet another section of the display 72 (indicated at 84) may change as well, to show or describe the section of the system 10 and/or fluid flow circuit 12 that is the location of the error/defect (e.g., showing a picture or illustration of a particular clamp or sensor).

One class of errors/defects leading to an alarm condition includes errors in the way that a fluid flow circuit 12 is associated with the system 10 and defects in the blood processing system 10 and/or a fluid flow circuit 12 that has been associated with the system 10. One such error may be either failing to associate a tubing line of the fluid flow circuit 12 with one of the pressure sensors, clamps, and/or pumps of the system 10 or improperly associating a tubing line with a sensor, clamp, or pump (e.g., by failing to close one of the pumps or transducer panels or installing a tubing line into the associated pump backwards). A similar error may involve transposing the tubing lines to be associated with a pair of sensors, clamps, and/or pumps of the system 10. Another error may involve failing to apply a hemostat or comparable clamping device to the source/recipient access line 22 when associating the fluid flow circuit 12 to the system 10. Yet another error may involve failing to replace a used fluid flow circuit 12 with a new fluid flow circuit 12. A defective fluid flow circuit 12 may have one or more leaks or obstructions in its tubing lines (or in another one of its other components), for example. A defective system 10 may have an improperly functioning sensor or a broken transducer panel, for example.

The way in which these errors/defects are detected may vary depending on the configuration of the system 10, the sensors it includes and their locations, and the testing protocol programmed into the controller 16. For example, in one embodiment, if the system 10 is provided with one or more weight scales and one or more of the weight scales registers a greater initial weight than is expected, it may be indicative of a failure to replace a used fluid flow circuit 12 (because fluid is already in the fluid flow circuit 12 before connecting a blood source). Failure to replace a used fluid flow circuit 12 may additionally or alternatively be identified by the air detection assembly 64 detecting fluid before a blood source has been connected to the system 10. The detection of fluid by the air detection assembly 64 prior to connection of a blood source may instead be indicative of a defect in the operation of the air detection assembly 64. The controller 16 may consider signals from a plurality of sensors (e.g., from both the air detection assembly 64 and one or more weight scales) to better diagnose the source of an error/defect. Additionally, information regarding the current state in progress at the time that an error/defect is identified (e.g., whether the system 10 is powering up versus actually carrying out a procedure) may help the controller 16 to better diagnose the source of an error/defect. Thus, it should be understood that the particular way in which an error/defect is identified may vary without departing from the scope of the present disclosure.

Typically, the response to the detection of an error or defect includes all of the clamps of the system 10 closing (if not already in a closed condition) to prevent fluid flow through the associated tubing line, which ensures that fluid is not transferred to the blood source or fluid recipient when there is a possible unsafe condition. However, the above class of errors/defects may be detected at a time when there is no blood source or fluid recipient connected to the system 10, such that it is not necessary to immediately close all or any of the clamps. For example, before a blood source is connected to the system 10, the system 10 must be powered on (which may be referred to as an initialization state) or, if the system 10 is being used several times consecutively without powering off, the system 10 must transition between consecutive uses (which may be referred to as an inter-procedure state) to place the system 10 in condition to have a new fluid flow circuit 12 associated therewith. Once the initialization or inter-procedure state has been completed, a fluid flow circuit 12 may be associated therewith (which may be referred to as an installation state), after which time the controller 16 and sensors cooperate to determine whether the fluid flow circuit 12 has been properly installed (which may be referred to as an installation verification state). When it has been determined that the fluid flow circuit 12 has been properly installed and that there are no defects in either the system 10 or the fluid flow circuit 12, the blood source (and fluid recipient, if different from the blood source) may be connected to the system 10 (which may be referred to as a connection state) and a procedure may be carried out by the system 10 (which may be referred to as a processing state).

After determining that there is an error/defect (e.g., one of the class described above) and before taking action with respect to any of the clamps of the system 10, the controller 16 may proceed to determine whether a selected system state exists. In particular, the controller 16 may check to confirm the absence of fluid connection to a blood source or fluid recipient (e.g., by confirming that one of the above pre-connection states is in progress). If the controller 16 confirms that the selected system state does not exist (e.g., if there is a fluid connection to a blood source or fluid recipient), then it may be advantageous for the controller 16 to cause one or more clamps (which may include all of the clamps) to automatically move to a closed condition (if not already in the closed condition) to prevent unintended fluid flow to the source/recipient and/or between fluid containers. However, if the controller 16 confirms that the selected system state does exist, then the controller 16 may take any of a number of possible actions with respect to the clamps. For example, in one embodiment, the controller 16 causes or allows the clamps to remain in the condition they were in (i.e., either closed or open) at the time that the error/defect was identified. This may be advantageous to allow an operator to check on an individual clamp if the error/defect involved a particular clamp not being in an expected condition (e.g., if a clamp fails to open or close when it should have). In another embodiment, the controller 16 may cause one or more of the clamps (which may include all of the clamps) to move from a closed condition to an open condition or, if already in the open condition, to remain in the open condition. In yet another embodiment, the controller 16 may cause one or more of the clamps (which may include all of the clamps) to move from an open condition to a closed condition or, if already in the closed condition, to remain in the closed condition. In another embodiment, the controller 16 may cause one or more clamps to move from a closed condition to an open condition and cause one or more other clamps to move from the open condition to the closed condition.

Additionally, if the controller 16 confirms that the selected system state exists, then it may be possible for one or more of the clamps to be selectively opened without the risk of fluid being transferred to a living blood source or fluid recipient when there is a possible unsafe condition. In this case, the change in appearance of the display 72 caused by the controller 16 may include displaying one or more interactive icons 86 (FIG. 9) in one or more sections of the display 72 (indicated at 88 in FIG. 8).

Figure 9:
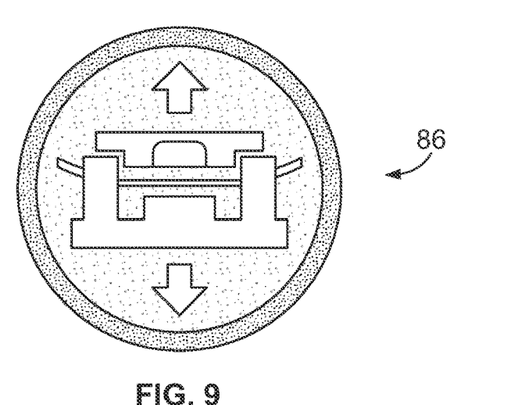
FIG. 9 illustrates an interactive icon of the display of FIG. 8, in an enabled condition.

The interactive icon 86 may be manipulated by the operator (e.g., by pressing the display 72 at the location of the icon 86, if the display 72 is a touchscreen) to move one or more of the clamps of the system 10 from the closed condition to an open condition. This may be advantageous to allow the operator to carry out the required recovery actions, which may include adjusting the way in which the fluid flow circuit 12 is associated with the system 10 (e.g., by allowing the operator to change the way in which a tubing line is associated with a pump or to replace a defective fluid flow circuit 12 with a new fluid flow circuit 12). This is an improvement upon certain known blood processing systems, in which an alarm condition must be closed in order to open the clamps of the system, which removes the required recovery actions from the display, thereby requiring an operator to remember the necessary recovery actions while carrying them out.

Figure 10:
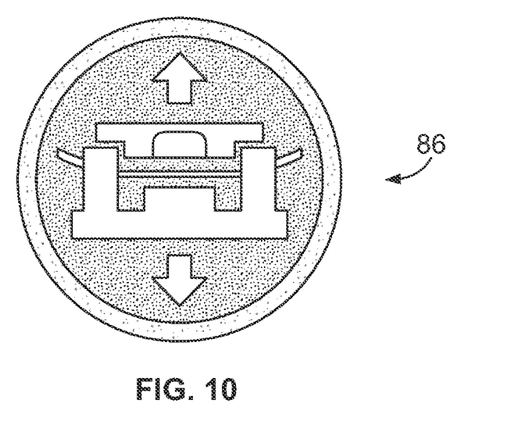
FIG. 10 illustrates the interactive icon of FIG. 9 in a pressed condition.
Figure 11:
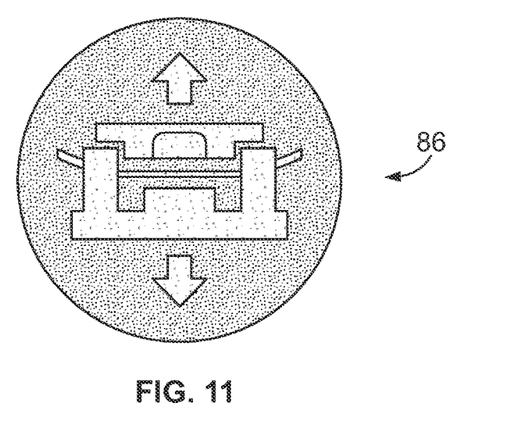
FIG. 11 illustrates the interactive icon of FIG. 9 in a disabled condition.

In one embodiment, the icon 86 is not visible before the controller 16 has determined that the selected system state exists, such that confirming the existence of such state and changing the appearance of the display 72 includes causing the icon 86 to appear. In another embodiment, the icon 86 is present at all times, but its appearance changes upon the controller 16 confirming the existence of the selected system state. For example, FIGS. 9-11 illustrate three different conditions that the icon 86 may move between according to one embodiment. It will be seen that the shape of the icon 86 is the same in all three conditions, but that only the color of the icon 86 differs to signify the current condition of the icon 86. In an enabled condition (FIG. 9), the icon 86 or at least a portion thereof may be primarily one color (e.g., green). In a pressed condition (FIG. 10), the icon 86 or at least that same portion thereof may be primarily a different color than in the enabled condition (e.g., blue or a darker shade of green). In a disabled condition (FIG. 11), the icon 86 or at least that same portion thereof may be primarily a third color to distinguish it from the enabled and pressed conditions (e.g., gray or red). It should be understood that the shape and colors of the illustrated icon 86 are merely exemplary and that other combinations of shapes and/or colors may be used without departing from the scope of the present disclosure. Furthermore, rather than changing only in color to distinguish between different conditions, an icon may change in only shape or in only size or in two or more ways (e.g., changing in shape and size or changing in shape and color or changing in color and size or changing in shape and size and color).

If the icon 86 may move between the three conditions, then it may start in the disabled condition of FIG. 11, before an error/defect has been identified. Additionally, the icon 86 may be in the disabled condition after an error/defect has been identified, if the selected system state does not exist (i.e., when there is an error/defect while a blood source or fluid recipient is connected to the system 10). When the controller 16 has determined there to be an error/defect and also determines that the selected system state exists (i.e., that there is no blood source or fluid recipient connected to the system 10), then the controller 16 may change the appearance of the display 72 by (among other things) causing the appearance of the icon 86 to change from the disabled condition of FIG. 11 to the enabled condition of FIG. 9. After the icon 86 has been manipulated to move the clamp or clamps from the closed condition to the open condition (or while the icon 86 is being manipulated), the controller 16 may cause the appearance of the icon 86 to change from the enabled condition of FIG. 9 to the pressed condition of FIG. 10. This may include the icon 86 changing to the pressed condition of FIG. 10 only while it is being manipulated, with the icon 86 thereafter automatically changing to another condition (e.g., the disabled condition of FIG. 11) when it is no longer being manipulated. In another embodiment, the icon 86 may remain in the pressed condition during and after being manipulated. In yet another embodiment, the icon 86 may move to the pressed condition only after having been manipulated (e.g., after an operator has removed their finger from the icon 86). For these latter two embodiments, when the error/defect has been resolved or at any other appropriate time, the controller 16 may cause the appearance of the icon 86 to change from the pressed condition of FIG. 10 to the disabled condition of FIG. 11. It is also within the scope of the present disclosure for the controller 16 to be programmed to change the appearance of the icon 86 from the pressed condition of FIG. 10 directly to the enabled condition of FIG. 9, if it is necessary for the clamp or clamps to be opened an additional time.

After carrying out the recovery actions necessary to address the error/defect, the operator may inform the controller 16 that the recovery actions have been performed (e.g., by pressing an interactive confirmation icon 90). Depending on the nature of the error/defect and the exact state in which the system 10 is in at the time of the error/defect being identified, the controller 16 may proceed in one of any of a number of ways. For example, the controller 16 may proceed by restarting the state in which the system 10 was in at the time of the error/defect being identified (e.g., if there is an error/defect identified during the installation verification state, the controller 16 may cause the installation verification state to be restarted, rather than restarting the earlier installation state). In another embodiment, the controller 16 may proceed by moving the system 10 to a different state after receiving confirmation that all of the recovery steps have been performed (e.g., by moving to the installation state after addressing an error/defect identified during the installation verification state).

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A graphical user interface of a durable blood processing system including a clamp and configured for use in combination with a disposable fluid flow circuit including a tubing line associable with the clamp, the graphical user interface comprising:
   a display; and
   a controller associated with the display, wherein the controller is programmed to determine the existence of an error in the way in which the fluid flow circuit is associated with the blood processing system and/or a defect in the fluid flow circuit and/or the blood processing system and, upon determining the existence of said error and/or defect,
   determine whether a selected system state exists, and
   cause a change in the appearance of the display to represent the existence of said error and/or defect, wherein, if the selected system state exists, the change in the appearance of the display includes displaying an interactive icon on the display that may be manipulated to cause the clamp to be moved from a closed condition to an open condition.

2. The graphical user interface of claim 1, wherein
   the change in the appearance of the display when the controller has determined that the selected system state exists comprises changing the appearance of the icon from a disabled condition to an enabled condition,
   a color of at least a portion of the icon is different in the disabled and enabled conditions, and the controller is configured to cause the appearance of the icon to change from the enabled condition to a pressed condition upon the icon being manipulated to cause the clamp to be moved from the closed condition to the open condition.

3. The graphical user interface of claim 1, wherein the controller is further programmed to, upon determining the existence of said error and/or defect, cause a change in the appearance of the display to represent one or more recovery actions to be performed to address said error and/or defect.

4. The graphical user interface of claim 1, wherein said selected system state comprises the absence of fluid connection to a blood source or a fluid recipient.

5. The graphical user interface of claim 1, wherein said selected system state comprises the operation of the blood processing system in an installation verification state to determine whether the fluid flow circuit has been properly associated with the blood processing system.

6. The graphical user interface of claim 5, wherein the controller is further programmed to restart the installation verification state after the icon has been manipulated to cause the clamp to be moved from the closed condition to the open condition.

7. The graphical user interface of claim 6, wherein the controller is further programmed to restart the installation verification state only after receiving a signal indicating that recovery actions have been performed to address said error and/or defect.

8. The graphical user interface of claim 1, wherein said selected system state comprises the operation of the blood processing system in an initialization state in which the blood processing system is powering on.

9. The graphical user interface of claim 8, wherein said error and/or defect comprises the failure to remove a used fluid flow circuit from the blood processing system and associate a new fluid flow circuit with the blood processing system.

10. The graphical user interface of claim 1, wherein said selected system state comprises the operation of the blood processing system in an inter-procedure state to determine whether the transition between consecutive uses of the blood processing system has been executed properly.

11. A method of monitoring the combination of a durable blood processing system including a clamp and a disposable fluid flow circuit including a tubing line associated with the clamp, the method comprising:
determining the existence of an error in the way in which the fluid flow circuit is associated with the blood processing system and/or a defect in the fluid flow circuit and/or the blood processing system;
upon determining the existence of said error and/or defect, determining whether a selected system state exists; and
if the selected system state exists, causing a change in the appearance of a display to represent the existence of said error and/or defect, wherein, the change in the appearance of the display includes displaying an interactive icon on the display that may be manipulated to cause the clamp to be moved from a closed condition to an open condition.

12. The method of claim 11, wherein
said displaying an interactive icon includes changing the appearance of the icon from a disabled condition to an enabled condition,
a color of at least a portion of the icon is different in the disabled and enabled conditions, and
manipulating the icon causes the appearance of the icon to change from the enabled condition to a pressed condition.

13. The method of claim 11, wherein said displaying an interactive icon includes displaying one or more recovery actions to be performed to address said error and/or defect.

14. The method of claim 11, wherein said determining whether a selected system state exists includes confirming the absence of fluid connection to a blood source or a fluid recipient.

15. The method of claim 11 wherein
said determining whether a selected system state exists includes determining whether an installation verification state is in progress, and
said installation verification state includes determining whether the fluid flow circuit has been properly associated with the blood processing system.

16. The method of claim 15, further comprising restarting the installation verification state after the icon has been manipulated to cause the clamp to be moved from the closed condition to the open condition.

17. The method of claim 16, wherein the installation verification state is restarted only after it has been confirmed that recovery actions have been performed to address said error and/or defect.

18. The method of claim 11, wherein
said determining whether a selected system state exists includes determining whether an initialization state is in progress, and
said initialization state includes powering on the blood processing system.

19. The method of claim 18, wherein said error and/or defect comprises the failure to remove a used fluid flow circuit from the blood processing system and associate a new fluid flow circuit with the blood processing system.

20. The method of claim 11, wherein
said determining whether a selected system state exists includes determining whether an inter-procedure state is in progress, and
said inter-procedure state includes determining whether the transition between consecutive uses of the blood processing system has been executed properly.

21. A blood processing system for use in combination with a disposable fluid flow circuit including a tubing line, the blood processing system comprising:
a graphical user interface comprising a display;
a clamp configured to be associated with the tubing line of the fluid flow circuit and movable between a closed condition in which fluid flow through the tubing line is prevented and an open condition in which fluid flow through the tubing line is allowed;
a controller associated with the display and with the clamp; and
a sensor associated with the controller, wherein the controller is programmed to
receive a signal from the sensor that is indicative of the existence of an error in the way in which the fluid flow circuit is associated with the blood processing system and/or a defect in the fluid flow circuit and/or the blood processing system and, upon receiving said signal from the sensor,
determine whether a selected system state exists, and
cause a change in the appearance of the display to represent the existence of said error and/or defect, wherein, if the selected system state exists, the change in the appearance of the display includes displaying an interactive icon on the display that may be manipulated to cause the clamp to be moved from the closed condition to the open condition.

22. The blood processing system of claim 21, wherein the change in the appearance of the display when the controller has determined that the selected system state exists comprises changing the appearance of the icon from a disabled condition to an enabled condition, and a color of at least a portion of the icon is different in the disabled and enabled conditions.

23. The blood processing system of claim 21, wherein the controller is configured to cause the appearance of the icon to change from an enabled condition to a pressed condition upon the icon being manipulated to cause the clamp to be moved from the closed condition to the open condition.

24. The blood processing system of claim 21, wherein the appearance of the icon may be changed between three conditions differing only in color.

25. The blood processing system of claim 21, wherein the controller is further programmed to, upon determining the existence of said error and/or defect, cause a change in the appearance of the display to represent one or more recovery actions to be performed to address said error and/or defect.

26. The blood processing system of claim 21, wherein said selected system state comprises the absence of fluid connection to a blood source or a fluid recipient.

27. The blood processing system of claim 21, wherein said selected system state comprises the operation of the blood processing system in an installation verification state to determine whether the fluid flow circuit has been properly associated with the blood processing system.

28. The blood processing system of claim 27, wherein the controller is further programmed to restart the installation verification state after the icon has been manipulated to cause the clamp to be moved from the closed condition to the open condition.

29. The blood processing system of claim 28, wherein the controller is further programmed to restart the installation verification state only after receiving a signal indicating that recovery actions have been performed to address said error and/or defect.

30. The blood processing system of claim 21, wherein said selected system state comprises the operation of the blood processing system in an initialization state in which the blood processing system is powering on.

31. The blood processing system of claim 30, wherein said error and/or defect comprises the failure to remove a used fluid flow circuit from the blood processing system and associate a new fluid flow circuit with the blood processing system.

32. The blood processing system of claim 21, wherein said selected system state comprises the operation of the blood processing system in an inter-procedure state to determine whether the transition between consecutive uses of the blood processing system has been executed properly.

33. The blood processing system of claim 21, wherein the sensor comprises a pressure sensor, a weight scale, an optical sensor, or an acoustic sensor.

\* \* \* \* \*